United States Patent [19]

Ashby et al.

[11] Patent Number: 5,189,222
[45] Date of Patent: Feb. 23, 1993

[54] PROCESS FOR THE MANUFACTURE AND RECOVERY OF ALKALI-METAL TETRAORGANYLBORATES

[75] Inventors: Eugene C. Ashby, Atlanta; Laurence L. Earnhart; Daniel W. Tedder, both of Marietta; Jagvir Singh, Smyrna, all of Ga.

[73] Assignee: Optima Chemicals, Inc., Douglas, Ga.

[21] Appl. No.: 472,330

[22] Filed: Jan. 29, 1990

Related U.S. Application Data

[63] Continuation-in-part of Ser. No. 26,050, Mar. 16, 1987, abandoned.

[51] Int. Cl.$^5$ ............................................... C07F 5/02
[52] U.S. Cl. ...................................................... 568/1
[58] Field of Search ........................................... 568/1

[56] References Cited

FOREIGN PATENT DOCUMENTS 0153885  4/1985  European Pat. Off. .

Primary Examiner—Marianne Cintins
Assistant Examiner—Margaret Argo
Attorney, Agent, or Firm—Hurt, Richardson, Garner, Todd & Cadenhead

[57] ABSTRACT

Process for the manufacture and recovery of alkali-metal tetraorganylborates. A mixed solvent and liquid/liquid contactor configuration is used in the system which aids in the recovery of the product.

53 Claims, 5 Drawing Sheets

PROCESS FOR THE MANUFACTURE AND RECOVERY OF ALKALI-METAL TETRAORGANYLBORATES

BACKGROUND OF THE INVENTION

This application is a continuation-in-part application of application Ser. No. 07/026,050, filed on Mar. 16, 1987 now abandoned.

The invention relates to the manufacture and recovery of alkali-metal tetraorganylborates, such as sodium tetraphenylborate. Specifically, the invention makes use of a solvent pair including a complexing agent (tetrahydrofuran) and an aromatic compound (toluene) which facilitates the recovery of the alkali-metal tetraorganylborate.

Tetraorganylborate compounds are useful for binding with specific radioactive material, i.e. cesium-137, and can be used to separate radioactive material from its carrier mass, therefore reducing significantly the amount of radioactive bulk. In practice, one use for tetraorganylborate compounds is to greatly reduce the mass and volume of radioactive wastes in, for example, disposal applications. The process can also be used for making other alkali metal tetraakyl- and tetraarylborates, trialkyl- and triarylborate- and alkyl and aryl Grignards.

Prior art methods for manufacturing alkali-metal tetraorganylborates typically use solvents consisting of 100% tetrahydrofuran (THF) or diethyl ether. Most prior art processes also require the use of waste evaporators, because of inefficient water economy, and those prior art processes using 100% THF as the solvent typically require two distillation columns to operate in order to break the tetrahydrofuran (THF) and water azeotrope. The lack of aqueous waste treatment by liquid/liquid extraction usually results in high product losses. Such prior art systems also exhibit less efficient raw material usage and are unable to recycle brine effectively without creating secondary wastes. Also, the prior art systems typically yield a product with a much lower purity, and the product must be recovered directly from a solvent stream.

U.S Pat. No. 3,405,179 discloses a process for producing a triarylborane by reacting an aryl Grignard reagent with boron trifluoride. An inert hydrocarbon solvent is also disclosed. Inert hydrocarbon solvent systems without ethers present for preparation of Grignard reagents are known but are typically hard to initiate, give low yields and the product tends to precipitate which makes it difficult to handle. In contrast, the process of the present invention initiates easily, yields virtually all of the alkali-metal tetraorganylborate produced in the manufacturing step, and yields this product in an aqueous raffinate.

U.S. Pat. No. 3,475,496 teaches the use of Grignard reagents with boron trifluoride. A triarylborane is produced through the concurrent or simultaneous formation of a Grignard reagent and its reaction with a boron compound. The process of the present invention requires the use of a three reactor sequences which make possible dedicated usage for and recovery of each intermediate product in the alkali-metal tetraorganylborate manufacturing step. Thus, reactor 112 of the present invention is used solely for Grignard production and a heel is left after each run to provide activated magnesium to allow immediate re-initiation of the next Grignard. Reactors 112 and 122 of the present invention are kept dry at all times and do not have to be cleaned of water and solids each cycle.

U.S. Pat. No. 4,510,327 relates to the preparation of alkali-metal tetraorganylborate compounds by reacting triorganylboranes with alkali-metal hydroxide or alkoxide compounds. Solvents may be used, but are not required. In this process it is necessary to first prepare triorganylboranes which usually are not available commercially and are difficult to be converted to useful forms. Alkali-metal tetraorganylborates are produced and recovered by the process of the present invention in a novel process different from the above, which, as a consequence, avoids the above process' difficulties.

European Patent No. 0,153,885 discloses specific tetraarylborate-ammonium complexes and their uses as antifouling, antiseptic, and antifungal agents. The European Patent uses boron trifluoride diethyl etherate as the boron source, and toluene, used solely as a potential solvent component for separating the organic layer from the aqueous layer for product isolation. Furthermore, in the European patent, during the product isolation step the solvent is simply stripped down, leaving many impurities in the process. The disadvantage inherent in this patent is the use of liquid-liquid extraction techniques; therefore, only alkali metal tetraorganylboron compounds in the aqueous phase may be extracted, leaving behind impurities in the organic layer.

SUMMARY OF THE INVENTION

It is accordingly an object of the present invention to provide a process for the manufacture and recovery of alkali-metal tetraorganylborate which uses a simple reagent.

It is another object of the present invention to provide a process, as above, which does not require the application of heat to the product to facilitate recovery.

It is yet another object of the present invention to provide a process, as above, which eliminates the need for the disposal of brine solution as a byproduct of the process.

It is still another object of the present invention to provide a process, as above, in which solvent loss is minimized.

It is yet another object of the present invention to provide a process, as above, in which the alkali-metal tetraorganylborate is recovered is an aqueous solution.

It is another object of the present invention to provide a process in which the alkali metal tetraorganylborate may be recovered in high purity in crystalline stage directly from an aqueous stream.

It is a further object of the present invention to provide a process in which purification and recovery of the product is done without heating.

It is still another object of the present invention to provide a process in which waste solution such as brine is recycled back to increase the product recovery.

It is also an object of the present invention to provide a process in which a waste product cake is created without an evaporator.

These objects and others set forth hereinafter, are achieved by a process for manufacturing and recovering an alkali-metal tetorganylborate (AMTOB) which comprises the steps of (1) manufacturing the AMTOB by (a) admixing magnesium, and an inert compound, and a complexing agent; (b) heating the mixture; (c) adding an organyl component and some more of the inert compound to the mixture, forming a Grignard reagent; (d) reacting the Grignard reagent with a borontrifluoride etherate to form a tetraorganylboromagnesium precipitate; and (e) reacting the precipitate with an alkali metal carbonate to form AMTOB, which is present in both an organic phase and an aqueous phase, and a salt precipitate; and then (2) recovering the AMTOB from the primary mixture of the organic phase, the aqueous phase, and the salt precipitate by (a) separating the organic phase from the primary mixture; (b) treating the aqueous phase and the salt precipitate with an organic solvent to cause the AMTOB to migrate from the aqueous phase and salt precipitate to the organic solvent; (c) separating the organic solvent containing the AMTOB from the aqueous phase and salt precipitate; and (d) extracting the AMTOB from the organic phase the organic solvent.

BRIEF DESCRIPTION OF THE DRAWINGS

For a full understanding of the true scope of the invention, the following detailed description should be read in conjunction with the drawings, wherein.

DETAILED DESCRIPTION OF THE PREFERRED EMBODIMENTS

Figure 1:
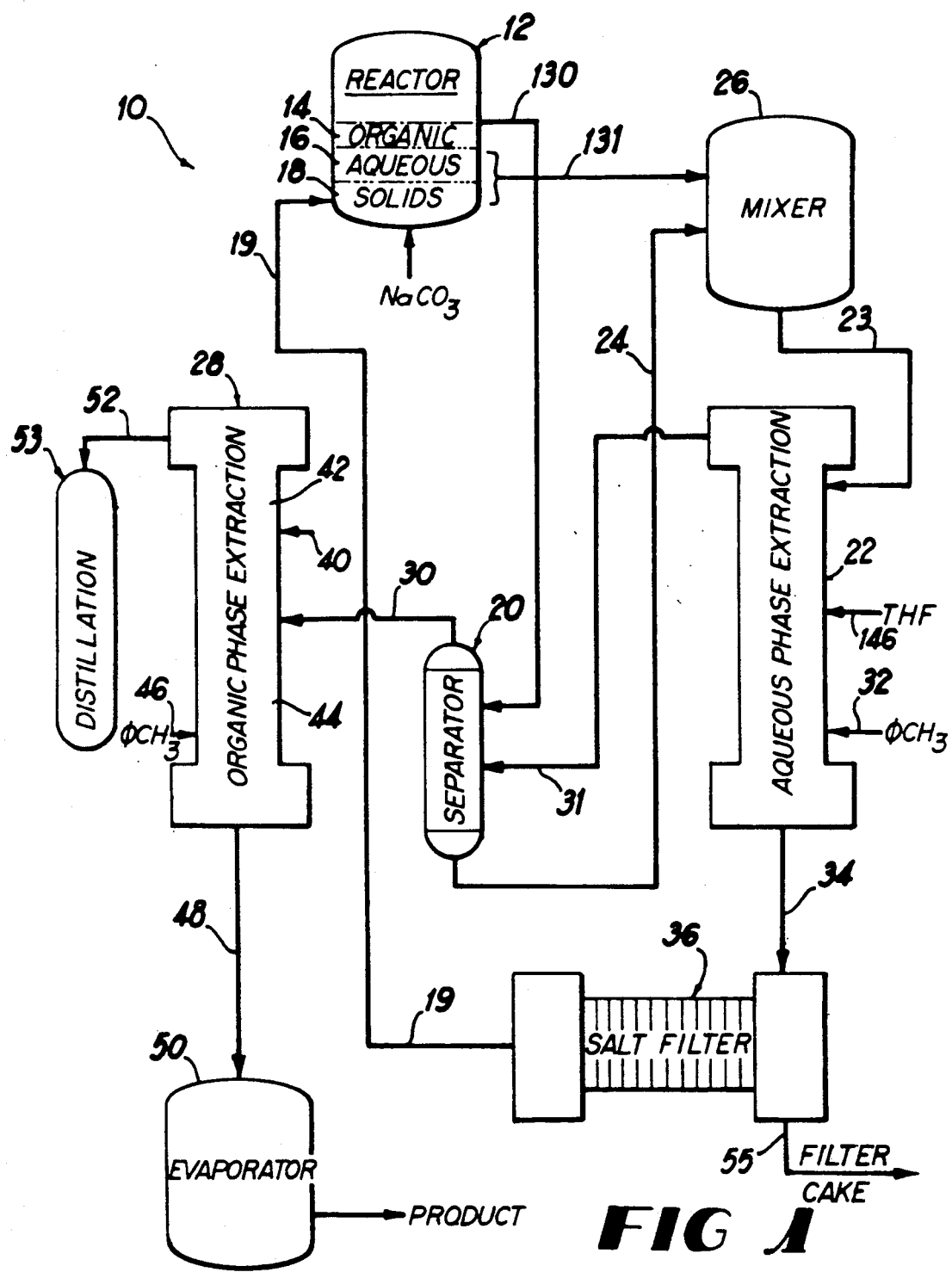
FIG. 1 is a simplified partial schematic of one embodiment of the process of the invention, illustrating the recovery portion of the process.

The process of the invention includes the following features (1) forming a precipitate for driving the reaction of the Grignard reagent, (2) using solvent mixtures to facilitate liquid/liquid extraction, (3) using solvent mixtures to control the product purity, (4) using liquid/liquid extraction columns to create a system which favors high product recoveries and purities without solvent evaporation prior to product recovery, (5) using brine recycle to achieve higher product recoveries and eliminate the need for a process waste evaporator, (6) blending solvents to obtain a suitable mixture for product recovery, (7) providing a method of product crystallization from an aqueous rather than solvent feed, (8) significantly reducing the need for using expensive ethers like tetrahydrofuran, (9) facilitating solvent recycle through the use of a single distillation column, and (10) a manufacturing sequence allowing the recovery of intermediate products.

The process of the invention is applicable to the manufacture and recovery of a wide variety of alkali-metal tetraorganylborates having the formula MBR$_4$ where M is an alkali metal selected from the group consisting of Li, Na, K, Cs and NH$_4$; and R is an organyl component from the group consisting of alkyls having from one to ten carbon atoms, and aryls and aralkyls having from six to fourteen carbon atoms.

One of the more widely manufactured alkali-metal tetraorganylborates is sodium tetraphenylborate (STPB). Other salts, such as tetraorganylammonium salts, are also possible to manufacture and recover using the present process and can be prepared in similar fashion. However, some salts, such as amonium salts, potassium salts, and cesium salts, have very limited solubility in water, and it would be impractical to use the extraction technology of the present invention to purify these salts, even though technically it is feasible.

The present process uses a mixed solvent pair which, in general, includes an aromatic compound and a compound which is capable of acting as a complexing agent for magnesium in the Grignard reaction. Examples of useful complexing agents include ethers, such as THF, diethyl ether, polycyclic ethers, etc., having from 2 to 12 carbon atoms; amines, such as trialkylamines and mono-, di-, and triamines, having from 1 to 18 carbon atoms; phosphines, such as trialkylphosphines, having from 3 to 18 carbon atoms; and organic sulfides, such as dialkyl sulfides, having from 2 to 12 carbon atoms.

In general, aromatic compounds suitable for use as one of the solvents have from six to ten carbon atoms in which any side chain pending from the phenyl ring is saturated such as, for example, toluene, benzene, diisopropyl benzene, or xylene. The aromatic compound acts as a diluent and must be non-reacting with the Grignard reagent.

For convenience, the following description of the manufacture and recovery of AMTOB utilizing an aromatic compound and a complexing agent as the solvent pair will include in parentheses, for example purposes only, the components used in the manufacture and recovery of sodium tetraphenylborate. It will be understood, however, that the process is applicable to the manufacture and recovery of alkali-metal tetraorganylborates generally, and to solvent systems other than the aromatic compound (toluene)/complexing agent (THF) system used as the parenthetical example.

FIG. 1 illustrates the various portions of a simplified partial schematic process diagram of one embodiment of part of the process of the invention, the overall process for recovery of AMTOB (STPB) is indicated generally by the number 10. A three-phase mixture which includes AMTOB (STPB) is contained in reactor vessel 12. This three-phase mixture is the end product of the AMTOB (STPB) manufacturing process which will be described in greater detail hereinafter. In the vessel 12 is an organic phase which includes a large portion of the AMTOB (STPB), together with aromatic compound or solvent (toluene) and complexing agent (THF), forms the top layer 14. Beneath this top layer 14 is an aqueous phase or middle layer 16 which also contains some AMTOB (STPB) and some complexing agent (THF), the latter being miscible with water, and some water. The bottom phase or layer 18 comprises solid salts and includes inter alia. magnesium carbonate salts, which are a by-product of the reaction for forming AMTOB (STPB) via a magnesium Grignard reagent.

The AMTOB (STPB) is present in both the organic phase or layer 14 and the aqueous phase or layer 16 in vessel 12. The presence of the salt precipitate solids into layer 18 and also provides that the aqueous phase 16 is salt saturated, thereby shifting the AMTOB (STPB) distribution coefficient (defined in connection with and illustrated in FIGS. 4 and 5) such that the bulk of the AMTOB (STPB) is in the organic phase or layer 14. The aqueous phase or layer 16, however, still contains appreciable amounts of AMTOB (STPB) as well as some complexing agent (THF). The aromatic compound (toluene) present in the organic phase or layer 14 of vessel 12 also serves to reduce the amount of salt contamination in organic phase or layer 14, since salts are soluble only in water and not in the aromatic compound or solvent (toluene).

The organic phase or layer 14 is decanted from vessel 12 to a separator 20. The addition of recycled brine 19, more fully discussed below, to the vessel 12 raises the organic phase/aqueous phase, liquid/liquid interface insuring that all of the organic phase or layer 14 up to this interphase is decanted to separator 20. However, decantation also may include partial decantation of the aqueous phase or layer 16 with the organic phase or layer 14. In separator 20 any aqueous phase 16 partially decanted with the organic phase 14 is separated from the organic phase 14 and introduced to a mixer 26. The aqueous phase 16 and the salt precipitate solids 18 are removed from vessel 12 and introduced directly into mixer 26. Some organic phase 14 may be removed from reactor 12 with the aqueous phase 16 and the solids 18 and introduced into mixer 26.

In mixer 26 the aqueous phase 16 and the solids 18 from the vessel 12 are combined and mixed with aqueous phase stream via conduit 24 from the separator 20. After aqueous phase 16, solids 18, and aqueous phase 24 are combined in the mixer 26, the combined mixture stream is introduced via conduit 23 into aqueous phase extraction column 22. Combined mixture stream 23 contains appreciable amounts of AMTOB (STPB) from aqueous phase 16 and aqueous phase 24, both of which contain AMTOB (STPB).

The AMTOB (STPB) in the combined mixture stream 23 is extracted using a complexing agent (THF) 146 introduced in the middle of column 22. Any excess complexing agent (THF) 146 is extracted using an aromatic compound (toluene) 32 entering column 22 below the entrance point of complexing agent (THF) 146. The extracted AMTOB (STPB), the excess complexing agent (THF), and the aromatic compound (toluene) exit column 22 as the tops product organic extract stream 31 which is then introduced into separator 20. The raffinate 34 of column 22 consists essentially of water and the salt precipitate solids 18 from vessel 22.

The raffinate 34 containing water and salt precipitate solids enters salt filter 36 which filters out the salt precipitate solids from the raffinate as a filter cake 55 leaving brine stream 19. The brine stream 19 exits filter 36 and is recycled to vessel 12 as described above. The filter cake 55 is removed from filter 36 and disposed of in any conventional manner. The brine recycle 19 is an important feature of the process 10 in that it avoids the need to have a waste evaporator and disposal means for the raffinate 34 apart from that required for the disposal of filter cake 55. Further, the use of the brine recycle 19 is the vessel 12 produces higher recoveries of AMTOB (STPB) in the organic phase 14 by raising the distribution coefficient of AMTOB (STPB) in the organic phase and the aqueous Phase such that the bulk of the AMTOB (STPB) migrates and is found in the organic phase 14.

The extraction with the mixed solvent pair of an aromatic compound (toluene) 32 and a complexing agent (THF) 146 in column 22, in addition to extracting AMTOB (STPB) from the aqueous phase, also substantially reduces salt contamination in the organic extract stream 31 by forcing water, which is miscible with the complexing agent (THF) 146 in the organic phase, from the organic phase to the aqueous phase. The organic extract stream 31 is thus "dried". The reduction of the amount of water in the organic extract 31 correspondingly reduces the amount of salt contamination in the organic extract 31 since the salts 18 are soluble only in water, not in complexing agent (THF) 146 or aromatic compound (toluene) 32. Therefore, virtually all of the salt 18 entering column 22 in combined mixture stream 23 exits as salt precipitate solids and in solution with water in raffinate stream 34.

The separator 20 now contains the organic phase 14 decanted from vessel 12, any aqueous phase 16 partially decanted with organic phase 14 during decantation, and the organic extract stream 31 from the aqueous phase column 22. The organic extract stream 31 contains virtually all of the AMTOB (STPB) originally contained in aqueous phase 16 of reactor vessel 12. Furthermore, the organic extract stream 31 is aromatic compound (toluene) rich as it consists mostly of aromatic compound (toluene) added as stream 32 in the aqueous phase extraction column 22. The complexing agent (THF) to aromatic compound (toluene) ratio in the organic extract stream 31 is from about 0.05 to about 0.4 on a weight basis. In separator 20, the aqueous phases contained in decanted stream 130 and the organic extract stream 31 are separated from the organic phases from decanted stream 130 and the organic extract stream 131. The aqueous phases exits the separator 20 as stream 24 and are introduced to the mixer 26 as described above. The organic phases are removed from the separator 20 as stream 30 and are introduced into the middle of organic phase extraction column 28.

The AMTOB (STPB) is extracted in organic phase extraction column 28 by adding water 40 as a stream above the addition point of the organic phase stream 30. By increasing the ratio of water to complexing agent (THF) the AMTOB (STPB) migrates to the water stream and leaves the column 28 as the aqueous raffinate 48. The excess complexing agent (THF) is brought into column 28 by stream 30 is extracted using an aromatic compound (toluene) 46 entering column 28 below the addition point of organic phase stream 30. The organic phase separated in column 28 is a mixed solvent phase consisting essentially of a pure solvent mixture of complexing agent (THF) from organic phase 30 and aromatic compound (toluene) 46. The organic phase exits column 28 as stream 52 and is recycled for use in the entire process 10 after appropriate conventional distillation treatment in distillation column 53. Organic phase stream 52 is aromatic compound (toluene) rich having an aromatic compound (toluene) to complexing agent (THF) ratio of from about 0.5 to about 0.15 on a weight basis.

The aqueous raffinate 48, which contains virtually all of the AMTOB (STPB) originally introduced to the process 10 exits organic phase extraction column 28 and proceeds to evaporator 50 where any residual amounts of solvents (aromatic compound and complexing agent) are evaporated. The product stream exiting evaporator 50 is essentially pure AMTOB (STPB) which can then be subjected to a number of treatments depending on customer specifications. For example, the AMTOB (STPB) can be shipped in its aqueous form or, alternatively, it can be crystalized and shipped in its crystalized form.

The advantages of the above-described recovery process include: (1) AMTOB (STPB) product is recovered in an aqueous Phase or solution rather than in an organic solution; (2) only a single distillation column is needed as the need for product recovery from a solvent phase (e.g. stream 130) using evaporation/distillation (not shown in FIG. 1) is eliminated by the aqueous phase medium for the final product; (3) crystallization of AMTOB (STPB) is much easier, safer, and less costly when performed on an aqueous solution; and (4) the transfer of the AMTOB (STPB) from the organic phase to the aqueous phase is performed without any solvent evaporation or heating of the product.

Figure 2:
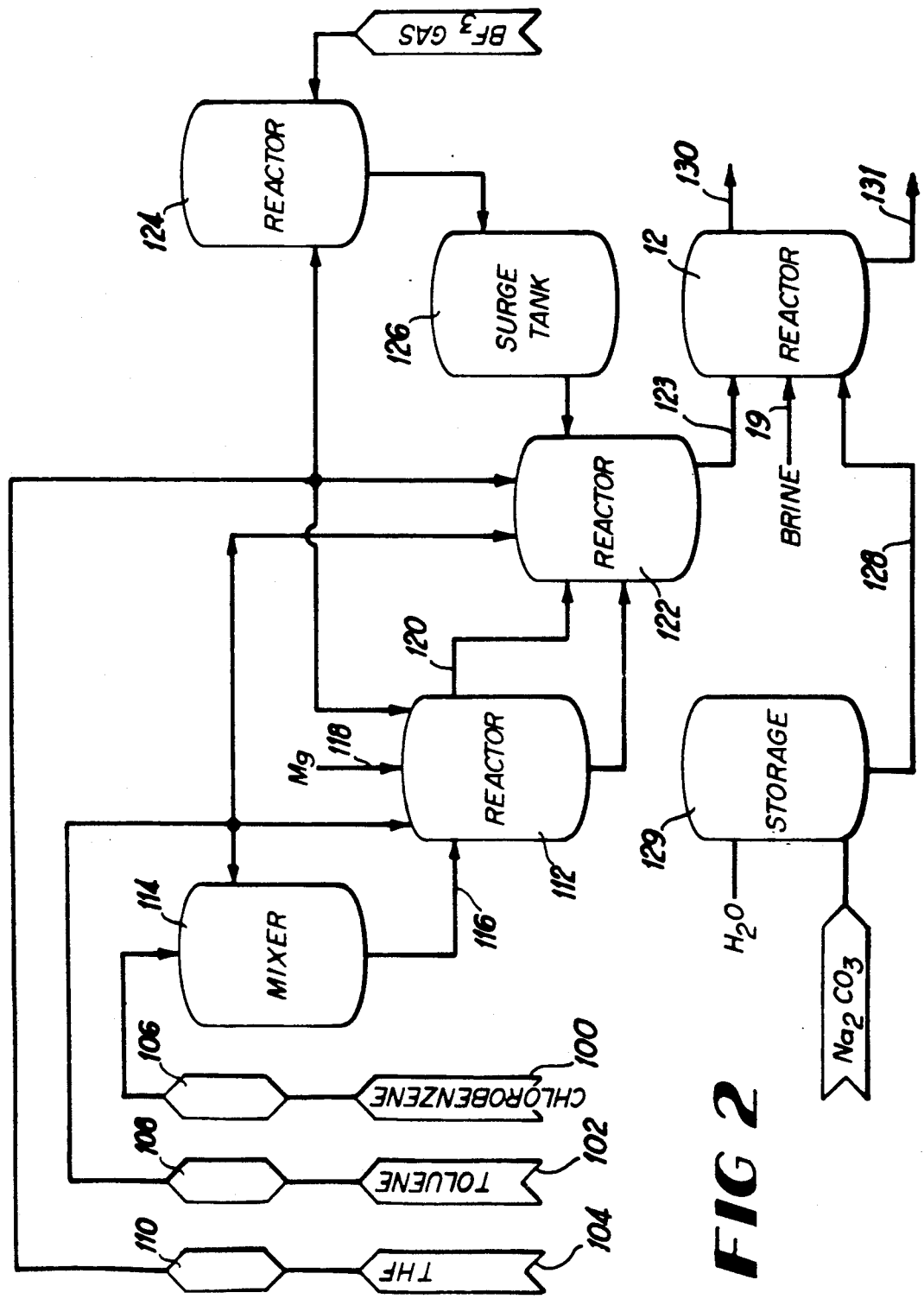
FIG. 2 is a detailed schematic of a portion of the process of the invention which includes manufacture of the Grignard reagent and reaction to form an alkalimetal tetraorganylborate.

FIG. 2 illustrates the various portions of a detailed schematic process diagram of one embodiment of the reaction steps for making AMTOB (STPB) via a Grignard reagent. Chlorobenzene stream 100 is a reagent that is consumed in forming the Grignard reagent. An aromatic compound (toluene) and a complexing agent (THF), streams 102 and 104, respectively, are from solvent recycle from the AMTOB (STPB) recovery process described above. Additional aromatic compound (toluene) and complexing agent (THF) are added as necessary. Streams 100, 102, 104 are passed through molecular sieve beds 106, 108, 110, respectively, or other drying apparatuses, for final drying in preparation for the AMTOB (STPB) manufacturing process.

The Grignard reagent is formed in a first reactor 112 by the following sequence of steps. First, a first portion of the aromatic compound (toluene) 102 and all of the chlorobenzene 100 are mixed in mixing vessel 114. Elemental magnesium 118, a second portion of the aromatic compound (toluene) 102, and a first portion of the complexing agent (THF) 104 are added directly to the first reactor 112. The resultant mixture is heated to a temperature of from about 50° to about 110° C. The first portion of the aromatic compound (toluene) and all of the chlorobenzene which were mixed in mixing vessel 114 are then added to a first reactor 112 via stream 116. The reaction of the elemental magnesium 118, the second portion of the aromatic compound (toluene), and the first portion of the complexing agent (THF) with the chlorobenzene-aromatic compound (toluene) mixture 116 forms the Grignard reagent which both is soluble in and forms a complex with the complexing agent (THF). Generally the solvent ratio of aromatic compound (toluene) to complexing agent (THF) is from about 0.5 to about 0.9 on a weight basis in the first reactor 112.

The formation of the Grignard reagent by the above process is well-known except for the use of a mixed solvent. That is, prior art processes for forming Grignard reagents involve the use of one solvent acting as a complexing agent, such as (THF) individually. The process of the present invention employs the novel use of a mixed solvent, that is, more specifically, a complexing agent (THF) and an aromatic compound (toluene).

The boron trifluoride etherate necessary for reaction with the Grignard reagent for the formation of the intermediate product tetraphenylboromagnesiumchloride (TPMgCl) is formed in a second reactor 124. First, a second portion of the complexing agent (THF) 104 is added to the second reactor 124. Second, boron trifluoride gas (BF$_3$) is metered in below the surface of the complexing agent (THF) in the second reactor 124. The BF$_3$ gas bubbles through and reacts with the complexing agent (THF) 104 to form the boron trifluoride etherate which is a complex between the complexing agent (THF) and the boron trifluoride. The boron trifluoride etherate is a liquid which is transferred from the second reactor 124 to a surge tank 126.

The Grignard reagent formed in the first reactor 112 is conveyed via an overflow stream 120 to a third reactor 122. The boron trifluoride etherate in surge tank 126 then is metered into the third reactor 122. Careful metering of the boron trifluoride etherate is required since the reaction of the boron trifluoride etherate with the Grignard reagent is very exothermic. The Grignard reagent reacts with the boron trifluoride etherate to form tetraphenylboromagnesiumchloride (TPBMgCl) as a precipitate. After this reaction has been completed, that is, when all of the boron trifluoride etherate has been metered into the third reactor 122 to react with the Grignard reagent, the contents of the third reactor 122 are dumped into reactor vessel 12 via stream 123. Vessel 12 is the initial reactor situated at the beginning of the AMTOB (STPB) recovery process described above and more fully depicted in FIGS. 1 and 3.

In vessel 12, the TPBMgCl is reacted with an alkali metal (sodium) carbonate, which is added to vessel 12 in the form of an aqueous stream 128 from storage vessel 129. The TPBMgCl reacts with the alkali metal (sodium) carbonate to form the end product AMTOB (STPB) and the salt precipitate byproduct. After a suitable settling time, generally from about 60 minutes to about 120 minutes, organic phase 14 in reactor vessel 12 is decanted, as previously described, through stream 130, to separator 20 (shown in FIGS. 1 and 3) while the aqueous phase 16 and salt precipitate 18 are conveyed out via stream 131 to mixer 26 (shown in FIGS. 1 and 3). The salt precipitate includes not only magnesium carbonate, but also alkali metal (sodium) fluoride and alkali metal (sodium) chloride.

Figure 3:
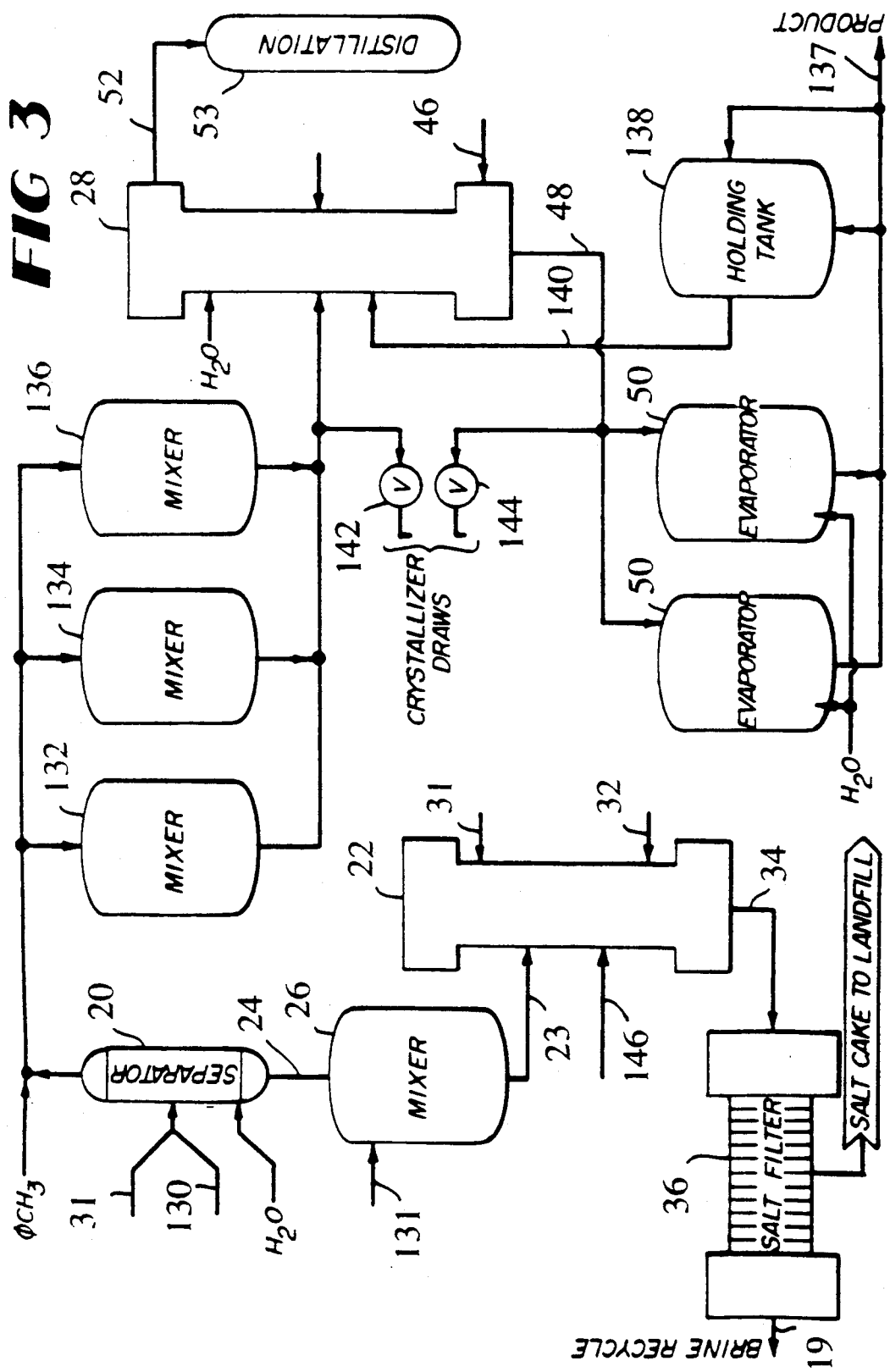
FIG. 3 is a detailed schematic of a second portion of the invention illustrating the extraction of the alkali-metal tetrorganylborate from an organic phase and from an aqueous phase.

Turning now to FIG. 3, the AMTOB (STPB) recovery Process, described above, is shown in more detail. The aqueous phase 16 and the solid salt precipitate 18 are combined with the aqueous phase stream 24 from separator 20 in mixing vessel 26 to form the aqueous stream 23 as described previously. Aqueous stream 23 is then introduced into the middle of the aqueous phase extraction column 22. Aqueous stream 23 contains relatively small amounts of AMTOB (STPB), that is from about 0.1 to about 0.2 weight percent of the aqueous feed 23 but enough to require recovery in column 22. The complexing agent (THF) 146 is introduced to column 23 below the entrance point of aqueous feed 23. Some aromatic compound (toluene) is contained in the complexing agent (THF) 146 in the form of the complexing agent (THF)-aromatic compound (toluene) azeotrope. The AMTOB (STPB) is transferred from the aqueous feed stream 23 to the mixed solvent, namely, the complexing agent (THF) and the aromatic compound (toluene), and exits the column 22 via organic extract stream 31. The solid salts entering column 22 via aqueous feed 23 exit column 22 as an aqueous raffinate 34 consisting essentially of water and the solid salt precipitate. After the solid salts have been removed in salt filter 36 as a solid salts cake 55, the brine 19 is recycled to vessel 12. Recycling the brine 19 to the vessel 12 produces a higher distribution coefficient between the aqueous phase 16 and the organic phase 14 so as to force the transfer of the majority of the AMTOB (STPB) from the aqueous phase 16 to the organic phase 14 in vessel 12. Adjustment of the complexing agent (THF)/aromatic compound (toluene) ratio in column 22 also affects the distribution coefficient. Preferably the ratio of complexing agent (THF)/aromatic compound (toluene) in column 22 should be from about 0.05 to about 1.0 by weight.

The organic extract stream 31 leaving as the tops product of column 22 generally has a concentration of from about 0.2 to about 4.0 percent by weight of AMTOB (STPB). Stream 31 is introduced to separator 20 where it mixes with organic phase 14 from vessel 12. As described above, the organic phase is separated from the aqueous phase in separator 20 with the aqueous phase being cycled to mixer 26 and the organic phase leaving as the tops product via organic phase stream 30. Organic phase stream 30 then passes to one of a plurality of mixing tanks 132, 134, 136 in which the ratio of the aromatic compound (toluene) to the complexing agent (THF) is adjusted to from about 1.6 to about 2.6. When this ratio has been achieved, the organic phase stream 30 is introduced to the middle of organic phase extraction column 28.

The AMTOB (STPB) is removed from the organic phase stream 31 in the organic phase extraction column 28 as described previously. The AMTOB (STPB) leaves column 28 in aqueous phase stream 48. After passing through one a plurality of evaporators 50, the AMTOB (STPB) is stored in one or more holding tanks 138 from which either it can be removed as a product stream 137 or it can be recycled to column 28 via stream 140 to provide a more concentrated product should the product stream 137 be of specification.

The AMTOB (STPB) can also be removed from the process as a crystalized product. This can be effected in two manners. In the first, a portion of aqueous raffinate 48 is directed to crystalizer 144 where the AMTOB (STPB) is crystalized out. In the second, a portion of the organic phase stream 30 from the separator 20 is introduced to crystalizer 142 where the AMTOB (STPB) is crystalized out.

The ability to recover AMTOB (STPB) from an aqueous phase is a tremendous advantage over the prior art since there is a reduced need for solvent recovery or disposal of non-aqueous waste streams.

Figure 4:
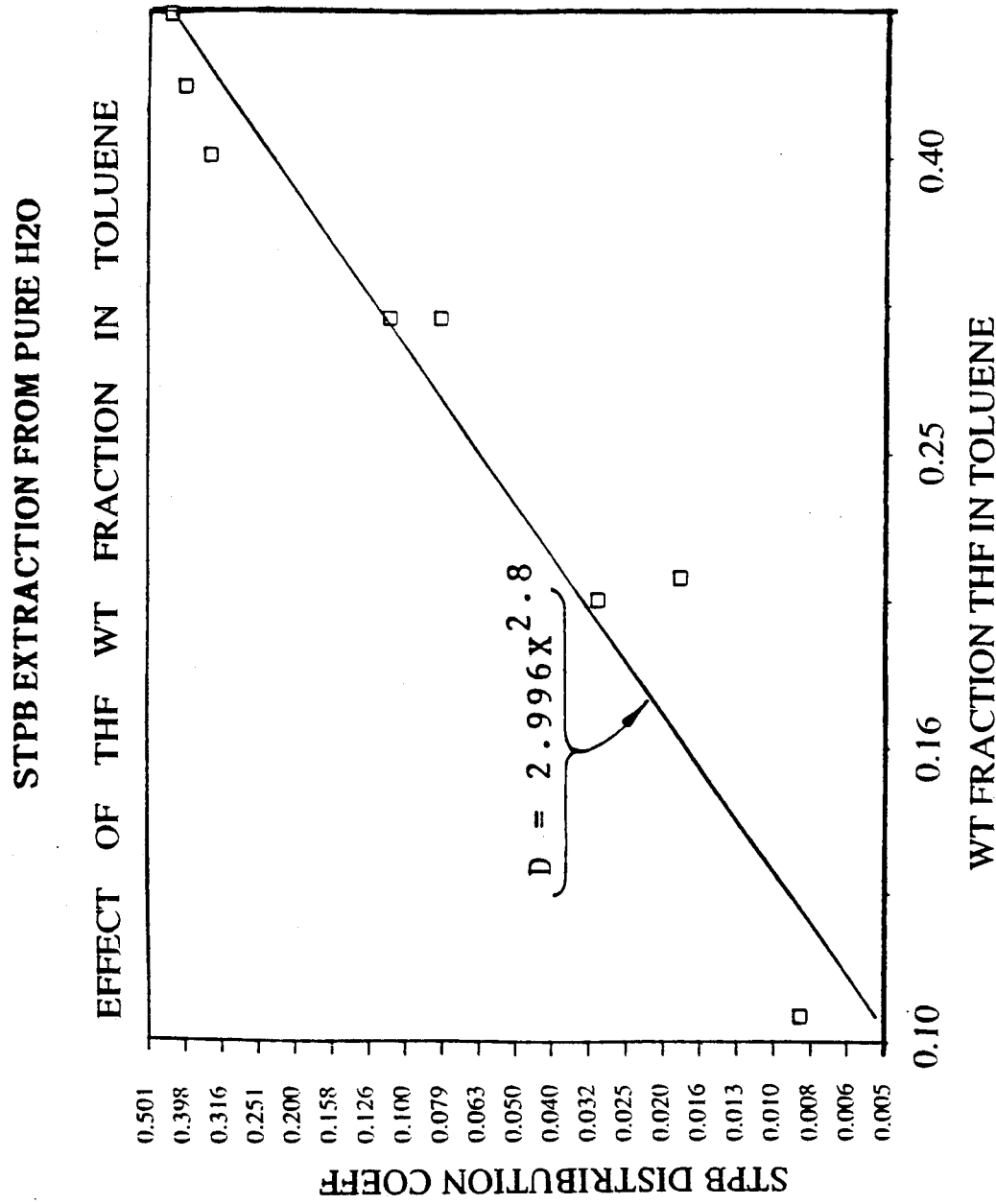
FIG. 4 is a graph of the distribution coefficient for sodium tetraphenylborate (STPB)
Figure 5:
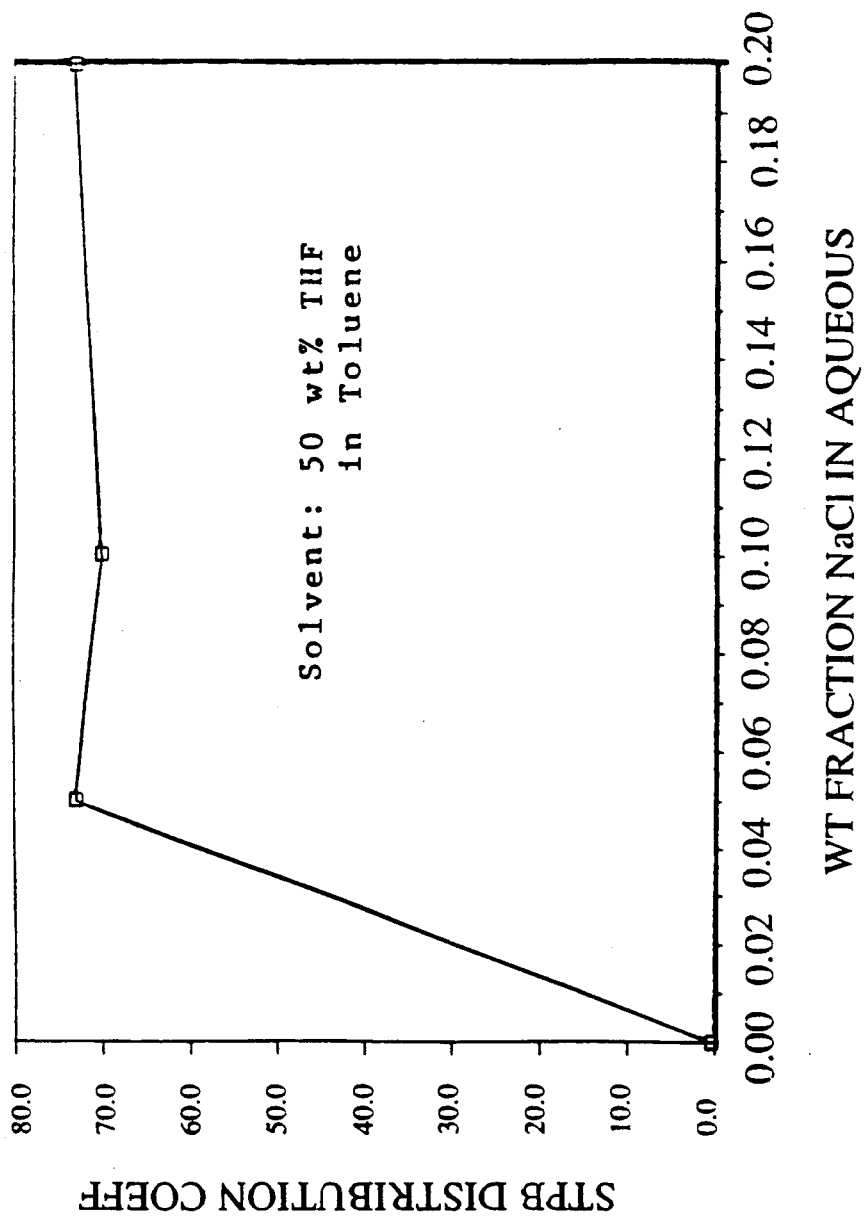
FIG. 5 is a graph of the STPB distribution coefficient as a function of the weight fraction of salt in aqueous solution.

FIGS. 4 and 5 are representative graphs of one AMTOB, STPB, extraction from pure H₂O and from salted aqueous phases, respectively. FIG. 4 illustrates the distribution coefficient for STPB (AMTOB) as a function of the weight fraction of THF (complexing agent) and toluene (aromatic compound) between the solvent phase and water (i.e. the aqueous phase containing only STPB salt). The THF (complexing agent) effect can be described by the equation:

$$D = 2.996 \, X^{2.8}$$

where the distribution coefficient D is expressed as the ratio of the grams per liter of STPB (AMTOB) in the organic layer divided by the grams per liter of STPB (AMTOB) in the aqueous layer at equilibrium. The X variable is the weight fraction THF (complexing agent) in the organic layer. This equation is the result of reducing the data of FIG. 4 to equation form.

In general, the high salting conditions in column 22 increase the AMTOB (STPB) distribution coefficient between the aqueous phase and the organic phase, thus making it easier to strip the aqueous layer of AMTOB (STPB) while maintaining low complexing agent (THF) concentrations in the solvent at that point. As mentioned previously, and as described more fully below, the "solvent" used in this process is a novel mixed solvent consisting essentially of an aromatic compound (toluene) and a complexing agent (THF). Mixing the primary reactor 12 extract, namely, organic phase 14 which is complexing agent (THF) rich, with the organic extract stream 31 from column 22 in the separator 20 reduces the complexing agent (THF) weight fraction in the composite feed to column 28 which helps the back extraction of the complexing agent (THF) in the aqueous layer of column 28.

The use of a mixed solvent results in much higher chloride and fluoride decontamination levels when compared to the use of 100% complexing agent (THF) as the solvent. This is due to the fact that the use of a second solvent, such as an aromatic compound (toluene), produces a "drier" organic phase, as mentioned above, by reducing the miscibility of the complexing agent (THF) and water in the organic phase, thereby forcing the water into the aqueous phase. Since the salt 18 is soluble only in the aqueous phase, the salt contamination of the organic layer 14 is reduced. Hence, the mixed solvent enables the production of a high purity AMTOB (STPB) product as well as higher recoveries. Finally, the connection of the solvent extraction columns, 22, 28 and the mixed solvent, enable AMTOB (STPB) recovery and purification without heating the mixed solvent in any way. Since AMTOB (STPB) is generally temperature sensitive, this feature helps to guarantee higher product yield.

FIG. 5 illustrates the STPB distribution coefficient as a function of the weight fraction of salt in the aqueous solution. As can be seen from this figure, salting of the aqueous phase forces a higher amount of the STPB into the organic phase.

The following values are the preferred ranges of the distribution coefficient (D) for the alkali-metal tetraorganylborates in a mixed solvent/water/salt system at various stages of the process. In vessel 12, D is from about 20 to about 50. In column 22, D is from about 50 to about 90 In column 28, D is from about 0.01 to about 0.2.

The ratio of solvents required to obtain the above distribution coefficients is a function of the particular solvents chosen and the particular alkali-metal tetraorganylborate being recovered. Those skilled in the art can readily determine the correct ratio of solvents given the above distribution coefficients.

What is claimed is:

1. A method of extracting an alkali metal tetraorganylborate from a primary mixture, the primary mixture being the end product of a process for producing the alkali metal tetraorganylborate, and said primary mixture comprising an aqueous phase containing alkali metal tetraorganylborate; an organic phase which is essentially immiscible in the aqueous phase, wherein the organic phase also contains alkali metal tetraorganylborate; and a solid phase, comprising the steps of:
   (a) separating the organic phase containing alkali metal tetraorganylborate both from the aqueous phase which also contains alkali metal tetraorganylborate, and from the solid phase;
   (b) treating the aqueous phase and the solid phase with an organic solvent to cause a portion of the alkali metal tetraorganylborate in the aqueous phase to migrate to and be contained in the organic solvent;
   (c) separating the organic solvent containing the alkali metal tetraorganylborate which has been separated from the aqueous phase and from the solid phase; and
   (d) extracting the alkali metal tetraorganylborate both from the organic phase and from the organic solvent, wherein said organic solvent comprises an inert compound and a complexing compound, said inert compound being selected from the group consisting of $C_{6-10}$arenes and $C_{5-8}$alkanes and said complexing compound being selected from the gorup consisting of $C_{2-12}$ethers, $C_{1-18}$amines, $C_{3-18}$phosphines and $C_{2-12}$sulfides.

2. The method as defined in claim 1 further comprising between steps (c) and (d), the step wherein the organic phase of the primary mixture and the organic solvent containing the alkali metal tetraorganylborate of step (b) are commingled.

3. The method as defined in claim 1 wherein the solid phase comprises salts, and including, after separating out the organic solvent containing alkali metal tetraorganylborate, filtering out salts in the solid phase and recycling the remainder of the solid phase to the primary mixture.

4. The method as defined in claim 2 including separating any residual aqueous phase and solid phase from the commingled organic phase and organic solvent and recycling the residual aqueous phase and solid phase to the aqueous phase and solid phase being treated with the organic solvent.

5. The method as defined in claim 1 including removing the alkali metal tetraorganylborate as an aqueous raffinate from the organic phase and the organic solvent.

6. The method as defined in claim 1 wherein the extracting of step (d) occurs simultaneously with the separating of step (c).

7. The method as defined in claim 1 including, after extracting the alkali metal tetraorganylborate from the organic phase and the organic solvent, distilling the organic phase and the organic solvent.

8. The method as defined in claim 1 including evaporating out any residual organic phase and organic solvent in the extracted alkali metal tetraorganylborate.

9. The method as defined in claim 1 wherein the organic phase comprises an inert compound, a complexing compound, and alkali metal tetraorganylborate; the aqueous phase comprises a complexing compound and alkali metal tetraorganylborate; and the solid phase comprises salts including magnesium carbonate salts.

10. The method as defined in claim 1 wherein the primary mixture is the end product of an alkali metal tetraorganylborate manufacturing process comprising the steps of:
(a) providing a quantity of magnesium, a quantity of the inert compound, and a quantity of the complexing agent;
(b) mixing the magnesium, a portion of the inert compound, and a portion of the complexing compound;
(c) heating the resultant mixture;
(d) adding a second mixture comprising an organyl component and a portion of the inert compound to the resultant mixture thus forming a Grignard reagent;
(e) reacting the Grignard reagent with a borontrifluoride etherate to form a tetraorganylboromagnesium precipitate; and
(f) reacting the tetraorganylboromagnesium precipitate with an alkali metal carbonate thereby forming alkali metal tetraorganylborate and salt precipitate including magnesium carbonate.

11. The method as defined in claim 9 wherein the inert compound has from six to ten carbon atoms.

12. The method as defined in claim 9 wherein the inert compound contains a phenyl ring and a saturated side chain pending from the phenyl ring.

13. The method as defined in claim 9 wherein the inert compound is non-reactive with a Grignard agent.

14. The method as defined in claim 9 wherein the inert compound is a diluent.

15. The method as defined in claim 9 wherein the inert compound is selected from the group consisting of aromatics, alkanes and their isomers and cyclic derivatives.

16. The method as defined in claim 15 wherein the inert compound is toluene.

17. The method as defined in claim 9 wherein the complexing compound is selected from the group consisting of ether, amine, phosphine, and sulfide.

18. The method as defined in claim 17 wherein the ether contains from two to twelve carbon atoms.

19. The method as defined in claim 17 wherein the amine is selected from the group consisting of $C_{1-18}$ trialkylamine, $C_{1-18}$ monoamine, $C_{1-18}$ diamine, and $C_{1-18}$ triamine.

20. The method as defined in claim 17 wherein the phosphine is a trialkylphosphine containing from three to eighteen carbon atoms.

21. The method as defined in claim 17 wherein the sulfide is a dialkyl sulfide containing from two to twelve carbon atoms.

22. The method as defined in claim 16 wherein the inert compound is toluene.

23. The method as defined in claim 1 wherein the extracted alkali metal tetraorganylborate product is in an aqueous solution.

24. The method as defined in claim 1 including crystallizing the extracted alkali metal tetraorganylborate.

25. The method as defined in claim 11 wherein the organyl component, the inert compound, and the complexing agent are dried prior to step (b).

26. The method as defined in claim 25 wherein the drying is accomplished usign molecular sieves.

27. The method as defined in claim 11 wherein the second mixture is produced simultaneously with the mixing of step (b).

28. The method as defined in claim 11 wherein the resultant mixture in step (c) is heated to a temperature of from about 50° C. to about 110° C.

29. The method as defined in claim 11 wherein the ratio of the inert compound to the complexing agent is from about 0.5 to about 0.9 on a weight basis.

30. The method as defined in claim 11 further comprising, between steps (d) and (e), the step of:
forming the borontrifluoride etherate by the reaction of borontrifluoride with a portion of the complexing agent.

31. The method as defined in claim 30 wherein the reaction proceeds by introducing borontrifluoride below the surface of the complexing agent.

32. The method as defined in claim 11 further comprising, between steps (d) and (e), the step of:
mixing a portion of the inert compound and a portion of the complexing agent with the Grignard reagent and the borontrifluoroide etherate.

33. The method as defined in claim 11 wherein the end product is allowed to settle.

34. The method as defined in claim 11 wherein the Grignard reagent is removed as a byproduct.

35. The method as defined in claim 11 wherein the tetraorganylboromagnesium is removed as a byproduct.

36. The method as defined in claim 30 wherein the borontrifluoride etherate is removed as a byproduct.

37. The method as defined in claim 11 wherein the alkali metal is selected from the group consisting of lithium, sodium, potassium, cesium, and ammonium.

38. The method as defined in claim 11 wherein the organyl component of said tetraorganylborate is selected from the group consisting of $C_{1-10}$ alkyl, $C_{6-14}$ aryl, and $C_{6-14}$ aralkyl.

39. The method as defined in claim 38 wherein the alkyl has from one to ten carbon atoms.

40. The method as defined in claim 38 wherein the aryl has from six to fourteen carbon atoms.

41. The method as defined in claim 38 wherein the aralkyl has from six to fourteen carbon atoms.

42. The method as defined in claim 11 wherein the inert compound has from five to ten carbon atoms.

43. The method as defined in claim 42 wherein the inert compound contains a phenyl ring and a saturated side chain pending from the phenyl ring.

44. The method as defined in claim 11 wherein the inert compound is non-reactive with the Grignard agent.

45. The method as defined in claim 11 wherein the inert compound is a diluent.

46. The method as defined in claim 42 wherein the inert compound is selected from the group consisting of aromatics, alkanes and their isomers and cyclic derivatives.

47. The method as defined in claim 11 wherein the complexing compound acts as a complexing agent in the Grignard reaction.

48. The method as defined in claim 11 wherein the complexing compound is selected from the group consisting of ehter, amine, phosphine, and sulfide.

49. The method as defined in claim 48 wherein the ether contains from two to twelve carbon atoms.

50. The method as defined in claim 48 wherein the amine is selected from the group comprising of $C_{1-18}$ trialkylamine, $C_{1-18}$ monoamine, $C_{1-18}$ diamine, and $C_{1-18}$ triamine.

51. The method as defined in claim 48 wherein the phosphine is a trialkyphosphine containing from three to eighteen carbon atoms.

52. The method as defined in claim 48 wherein the sulfide is a dialkyl sulfide containing from two to twelve carbon atoms.

53. The method as defined in claim 46 wherein the inert compound is toluene.

* * * * *